United States Patent
De Vocht et al.

(10) Patent No.: US 8,460,920 B2
(45) Date of Patent: *Jun. 11, 2013

(54) METHOD FOR THE PURIFICATION OF ADENOVIRUS PARTICLES

(75) Inventors: Marcel Leo De Vocht, Woerden (NL); Marloes Veenstra, Houten (NL)

(73) Assignee: Crucell Holland B.V., Leiden (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/501,721

(22) PCT Filed: Oct. 14, 2010

(86) PCT No.: PCT/EP2010/065430
§ 371 (c)(1), (2), (4) Date: Apr. 12, 2012

(87) PCT Pub. No.: WO2011/045378
PCT Pub. Date: Apr. 21, 2011

(65) Prior Publication Data
US 2012/0202267 A1    Aug. 9, 2012

Related U.S. Application Data

(60) Provisional application No. 61/279,014, filed on Oct. 15, 2009.

(30) Foreign Application Priority Data

Oct. 15, 2009 (EP) .................................. 09173090

(51) Int. Cl.
*C12N 1/02* (2006.01)
*C12N 15/00* (2006.01)
*A61K 39/00* (2006.01)
*A61K 39/23* (2006.01)

(52) U.S. Cl.
USPC ................... 435/261; 424/184.1; 424/233.1; 435/320.1

(58) Field of Classification Search
None
See application file for complete search history.

(56) References Cited

U.S. PATENT DOCUMENTS

| | | | |
|---|---|---|---|
| 5,559,099 A | 9/1996 | Wickham et al. | |
| 5,837,511 A | 11/1998 | Falck-Pedersen et al. | |
| 5,846,782 A | 12/1998 | Wickham | |
| 5,851,806 A | 12/1998 | Kovesdi | |
| 5,891,690 A | 4/1999 | Massie | |
| 5,965,541 A | 10/1999 | Wickham | |
| 5,981,225 A | 11/1999 | Kochanek | |
| 5,994,106 A | 11/1999 | Kovesdi | |
| 5,994,128 A | 11/1999 | Fallaux et al. | |
| 6,020,191 A | 2/2000 | Scaria et al. | |
| 6,040,174 A | 3/2000 | Imler et al. | |
| 6,113,913 A | 9/2000 | Brough et al. | |
| 6,492,169 B1 | 12/2002 | Vogels et al. | |
| 7,326,555 B2 | 2/2008 | Konz, Jr. et al. | |
| 2005/0153420 A1* | 7/2005 | Konz Jr. et al. ............... 435/239 |
| 2011/0207202 A1 | 8/2011 | Luitjens et al. | |

FOREIGN PATENT DOCUMENTS

| | | |
|---|---|---|
| EP | 1 230 354 | 1/2004 |
| WO | WO 96/26281 | 8/1996 |
| WO | WO 97/00326 | 1/1997 |
| WO | WO 97/08298 | 3/1997 |
| WO | WO 98/22588 | 5/1998 |
| WO | WO 98/39411 | 9/1998 |
| WO | WO 00/03029 | 1/2000 |
| WO | WO 02/44348 | 6/2002 |
| WO | WO 03/097797 | 11/2003 |
| WO | WO 03/104467 | 12/2003 |
| WO | WO 2004/099396 | 11/2004 |
| WO | WO 2005/080556 | 9/2005 |
| WO | WO 2005/095578 | 10/2005 |
| WO | WO 2006/108707 | 10/2006 |
| WO | WO 2008/006494 | 1/2008 |
| WO | WO 2010/060719 | 6/2010 |
| WO | WO 2011/045378 | 4/2011 |

OTHER PUBLICATIONS

Berdichevsky et al., Establishment of Higher Passage PER.C6 Cells for Adenovirus Manufacture; Biotechnol. Prog. 2008, 24, 158-165.
Cortin et al., High-Titer Adenovirus Vector Production in 293S Cell Perfusion Culture; Biotechnol. Prog. 2004, 20, 858863.
Fallaux et al., Characterization of 911: A New Helper Cell Line for the Titration and Propagation of Early Region -1 Deleted Adenoviral Vectors; Human Gene Therapy 7:215222; Jan. 20, 1996.
Goerke et al., Development of a Novel Adenovirus Purification Process Utilizing Selective Precipitation of Cellular DNA; published online May 11, 2005 in Wiley InterScience (www.interscience.wiley.com) 10 pages.
International Preliminary Report on Patentability; PCT/EP2010/065430 dated Feb. 28, 2012.
International Search Report; PCT/EP2010/065430 dated Jan. 26, 2011.
Maranga et al., Characterization of Changes in PER.C6™ Cellular Metabolism During Growth and Propagation of a Replication-Deficient Adenovirus Vector; published online Apr. 15, 2005 in Wiley InterScience (www.interscience.wily.com) 11 pages.
Yuk et al., Perfusion Cultures of Human Tumor Cells: A Scalable Production Platform for Oncolytic Adenoviral Vectors; published online Apr. 23, 2004 in Wiley InterScience (www.interscience.wiley.com) 6 pages.

* cited by examiner

*Primary Examiner* — Benjamin P Blumel
(74) *Attorney, Agent, or Firm* — TraskBritt

(57) ABSTRACT

The invention provides methods for large-scale adenovirus purification from high cell density suspensions, using host cell DNA precipitation followed by a clarification step.

11 Claims, 2 Drawing Sheets

METHOD FOR THE PURIFICATION OF ADENOVIRUS PARTICLES

CROSS-REFERENCE TO RELATED APPLICATION(S)

This is a national phase entry under 35 U.S.C. §371 of PCT International Patent Application PCT/EP2010/065430, filed Oct. 14, 2010, published in English as PCT International Publication WO 2011/045378 A1 on Apr. 21, 2011, which claims the benefit under Article 8 of the Patent Cooperation Treaty and 35 U.S.C. §119(e) to U.S. Patent Application Ser. No. 61/279,014 filed on Oct. 15, 2009 and under Article 8 of the Patent Cooperation Treaty to European Patent Application Serial No. 09173090.3 filed on Oct. 15, 2009.

The invention relates to the field of virus production. More particularly, it concerns improved methods for the purification of adenovirus particles from a cell suspension.

BACKGROUND OF THE INVENTION

Recent developments in the field of vaccine production have created the need for large scale manufacturing. Robust and high yield processes are needed to support the world with sufficient amounts of (recombinant) vaccines to combat infectious diseases.

Vaccines against infectious diseases can be based on recombinant adenovirus particles. For that reason, great efforts are being put into the optimization of cell based processes for adenovirus production. Cells are being cultured at increasing densities and subsequently infected in order to obtain higher total virus yields. Such high cell density processes are being disclosed in e.g. WO 2010/060719 of Crucell Holland BV, and in Yuk et al. (2004). A process for the production of large concentrations of recombinant adenovirus was described therein. This optimized process relies on the ability to infect cultures at high cell density (e.g. higher than $5 \times 10^6$ cells/ml) with preservation of a high virus productivity per cell. Herewith, it offers a method to obtain a harvested virus solution with high virus concentration in a single bioreactor. Typical virus particle (VP) yields of said processes are about $1.5–2.5 \times 10^{12}$ VP/mL.

Processes wherein cells are cultured at high densities are prone to the accumulation of high amounts of cell debris and host cell DNA. These contaminants have to be discarded further down the purification process, which is a cumbersome operation. A method for discarding host cell DNA from a harvested cell culture was disclosed previously in U.S. Pat. No. 7,326,555. The method consists of selectively precipitating host cell DNA away from the cell culture. A selective precipitating agent could specifically bind to host cell DNA and leave adenovirus particles unprecipitated. The method in this reference however has only been described for cell cultures with low cell density, wherein cell debris and host cell DNA are present in low quantities.

It was not known hitherto that said process could be applied in a culture containing high cell densities. To the contrary, from the prior art a strong suggestion could be inferred that a precipitating agent as used in said method would not selectively precipitate host cell DNA away from the culture and would precipitate virus particles when used at high concentrations (Goerke et al. 2004).

Since cell culture processes are being up-scaled and cells are being cultured at increasing densities, there is a need in the industry for downstream processes that enable the treatment of high cell density suspensions. This applies in particular to the field of adenovirus production.

SUMMARY OF THE INVENTION

The present invention relates to methods of purifying adenovirus particles from a cell lysate from a high cell density suspension. We have found herein that host cell DNA in high cell density suspensions could be selectively precipitated away from the lysed cell suspension, leaving viral particles unprecipitated. Selective precipitation of host cell DNA was performed with cationic detergents.

Selective precipitation in low cell density suspensions was previously described, for instance in U.S. Pat. No. 7,326,555. The achievement of selective precipitation in a high cell density suspension however was unprecedented and highly unexpected. Indeed, it was shown in the prior art, for instance in U.S. Pat. No. 7,326,555, that in low cell density suspensions (up to $1 \times 10^6$ cells/ml), adenovirus particles precipitate when the concentration of cationic detergent is increased. This suggests, based on extrapolation, that increasing the cationic detergent concentration in a substantial way (e.g. with a factor 2) would lead to precipitation of the totality of the adenovirus particles present in the suspension.

In high cell density suspensions, wherein the cell density is e.g. a ten-fold higher and thus the host cell DNA concentration is a ten-fold higher, it is expected that the concentration of detergent required for achieving the precipitation of host cell DNA would also be significantly higher. Hence, it would be expected, based on the results in low cell density suspensions, that such an increased concentration of detergent would have the effect of precipitating all the virus particles present in the solution.

During experimental testing at high cell densities (increased with a factor 10), we found that opposed to any suggestion or expectation based on the prior art, the increased concentration of cationic detergent (which was increased with a factor 2.5) did precipitate the host cell DNA (at least with 80%) but did not precipitate the adenovirus particles. Surprisingly, the selective precipitating effect of the detergent was maintained. Herewith, the present invention provides a process that can be used to discard host cell DNA in large scale adenovirus purification processes using high cell density cultures.

The invention provides a method for purifying adenovirus particles from a cell suspension containing between $5 \times 10^6$ and $150 \times 10^6$ cells per ml, the method comprising: a) lysing the cells within said cell suspension; b) selectively precipitating host cell DNA away from the adenovirus particles by addition of a selective precipitating agent; and c) clarifying said suspension containing said adenovirus particles to obtain a purified adenovirus-containing suspension wherein at least 80% of the host cell DNA is precipitated away from the adenovirus-containing suspension.

In some preferred embodiments said virus is purified from a cell suspension having a cell density ranging from $5 \times 10^6$ to $50 \times 10^6$ cells per ml, for instance $10 \times 10^6$ to $50 \times 10^6$ cells per ml or $10 \times 10^6$ to $30 \times 10^6$ cells per ml.

In certain embodiments, the selective precipitating agent used in step b) is a cationic detergent. In a preferred embodiment said selective precipitating agent is domiphen bromide (DB).

In certain embodiments, said selective precipitation agent is added to a concentration ranging from 1.2 to 5 mM. In a preferred embodiment said selective precipitation agent is added to a concentration ranging from 1.3 to 2.2 mM.

In certain embodiments, the method of the invention further comprises an anion-exchange step and an ultrafiltration step.

DETAILED DESCRIPTION OF THE INVENTION

Figure 1:
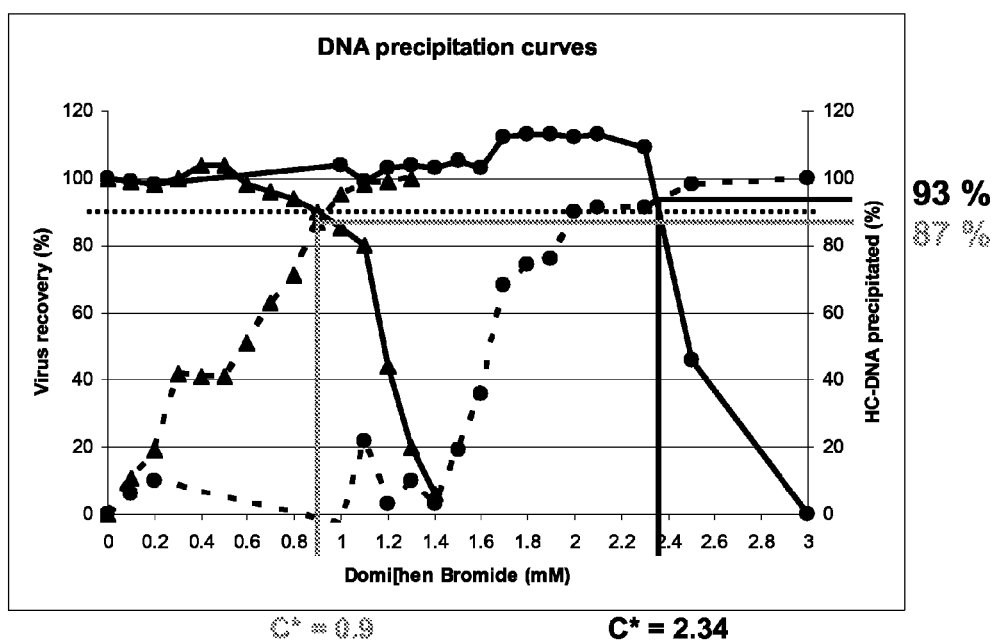
FIG. 1. Adenovirus recovery and precipitated host cell DNA, plotted against the domiphen bromide concentration in low ($2.5\times10^6$-$3.5\times10^6$ vc/ml) and high ($20\times10^6$-$30\times10^6$ vc/ml) density cell suspensions.

The present invention relates to methods of purifying adenovirus particles from a cell lysate from a high cell density suspension.

According to the invention, the high cell density suspensions are obtained by culturing cells to high cell densities. Such culturing can be performed in (not limited) batch, fed-batch or perfusion mode. Methods for culturing cells to high cell densities are known to the person skilled in the art. Specific methods for obtaining high cell density cultures are disclosed in e.g. WO2004/099396, WO2005/095578, WO2008/006494, WO 2010/060719.

According to the present invention, a high cell density suspension contains between about $5\times10^6$ and $150\times10^6$ cells/mL, e.g. between about $8\times10^6$ and $120\times10^6$ cells/mL, e.g. between about $12\times10^6$ and $100\times10^6$ cells/mL, e.g. between about $20\times10^6$ and $80\times10^6$ cells/mL.

In a preferred embodiment of the present invention, the cell density in said high cell density suspension ranges between about $10\times10^6$ and $50\times10^6$ cells/mL, e.g. at least about $15\times10^6$ cells/mL, e.g. at least about $20\times10^6$ cells/mL, e.g. at least about $25\times10^6$, e.g. up to about $30\times10^6$ cells/mL, e.g. up to about $35\times10^6$ cells/mL, e.g. up to about $40\times10^6$ cells/mL, e.g. up to about $45\times10^6$ cells/mL.

According to the present invention the high cell density cultures are subsequently infected with adenovirus particles in order to allow said adenovirus to propagate in the cell culture. Herewith, high cell density suspensions are obtained that contain high concentrations of adenovirus, in a single bioreactor. Methods for infecting high cell density cultures are known to the person skilled in the art. Specific methods for obtaining said high cell density cultures with high adenovirus concentration are disclosed in e.g. EP08168181.9, Cortin et al (2004), and Yuk et al (2004). These references describe processes for the production of large quantities of recombinant adenovirus. These processes rely on the ability to infect cultures at high cell density with preservation of a high adenovirus productivity per cell. Herewith, it offers a method to obtain a high cell density suspension with high adenovirus concentrations, in a single bioreactor. Typical yields of current processes e.g. for recombinant adenovirus 35 (rAd35) are about $1.5$-$2.5\times10^{12}$ VP/mL. Once the adenovirus has propagated in the cell culture, the adenovirus particles are, according to the present invention, purified from the high cell density suspension.

The method of the present invention in a first step includes lysing the cells contained in the high cell density suspension. Lysing high cell density suspensions, which were infected with adenovirus particles, cause large quantities of cell debris and host cell DNA to accumulate in the cell suspension. These accumulations render subsequent down stream processing of the cell suspension cumbersome.

The present invention provides a method suited for purifying adenovirus particles from the cell lysate of high cell density suspensions. Large quantities of host cell DNA are selectively precipitated away from the adenovirus particles within the high cell density suspension by adding a selective precipitating agent to the cell lysate such that at least about 80% of host cell DNA molecules are precipitated away from the high cell density suspension containing the adenovirus particles. As disclosed herein, the precipitation step allows for the precipitation of contaminating host cell DNA, with at least a 80% reduction in host cell DNA, preferably 90% and even more preferably, as exemplified herein, about a 95% reduction in host cell DNA following clarification (e.g. depth filtration).

Lysis

The first step of the process includes lysing the cells within the cell suspension. This first step, wherein the cell membranes are lysed, allows for the harvest of both cell-associated (intracellular) and non-associated (extracellular) adenovirus from the infected high cell density suspension. Host cell detergent lysis, while being the preferred method of lysing virus containing host cells, can be replaced by non-mechanical lysis methods (such as enzyme treatment) and/or mechanical shear methods (such as hollow fiber ultrafiltration) to release maximum amounts of adenovirus. Methods that can be used for active cell lysis are known to the person skilled in the art, and have for instance been discussed in WO 98/22588, p. 28-35. Useful methods in this respect are for example, freeze-thaw, solid shear, hypertonic and/or hypotonic lysis, liquid shear, sonication, high pressure extrusion, detergent lysis, combinations of the above, and the like. In one embodiment of the invention, the cells are lysed using at least one detergent. Use of a detergent for lysis has the advantage that it is an easy method, and that it is easily scalable.

Detergents that can be used, and the way they are employed, are generally known to the person skilled in the art. Several examples are for instance discussed in WO 98/22588, p. 29-33. Detergents, as used herein, can include but are not limited to anionic, cationic, zwitterionic, and nonionic detergents. Examples of detergents are for instance Triton and/or Polysorbate-80. In one embodiment, the detergent used is Triton X-100. In addition, a solvent such as TNBP can be added to the lysate or clarified lysate at low concentration to complement these detergents in their ability to inactivate enveloped viruses. Also, autolysis of the infected host cells by the adenovirus therein may provide for substantial release of intracellular adenovirus and may be used in the processes of the invention. Therefore, any form of host cell lysis which is known in the art may be used to liberate intracellular virus into the host cell culture medium for eventual harvesting by the methods disclosed herein. It is clear to the person skilled in the art that the optimal concentration of the detergent may vary, for instance within the range of about 0.1%-1% (w/w).

Selective Precipitation

Following lysis, DNA is selectively precipitated by addition of a concentrated selective precipitating agent (SPA) solution while leaving the adenovirus particles in the liquid phase. This step allows for the selective precipitation of host cell DNA and also improves downstream robustness. As exemplified herein, this early stage precipitation step results in about at least 80% reduction in (host cell) nucleic acid following clarification.

The SPAs which may be useful in practicing the present invention include, but are in no way limited to, amine copolymers, quaternary ammonium compounds, and any respective mixtures thereof. More specifically, the many forms of polyethylene (PEI) are very efficient in neutralization of excess anionic charge (DNA impurities). A list of possible SPAs that can be used appropriately in the present invention is given in U.S. Pat. No. 7,326,555 (column 12, lines 56-67 and column 13, lines 1-28), incorporated by reference herein. Appropriate SPAs for use in the present invention include but are not limited to the following classes and examples of commercially available products: monoalkyltrimethyl ammonium salts (examples of commercially available products include cetyltrimethylammonium bromide or chloride as CTAB, tetradecyltrimethylammonium bromide or chloride (TTA), alkyltrimethyl ammonium chloride, alkylaryltrimethyl ammonium chloride, dodecyltrimethylammonium bromide or chloride, dodecyldimethyl-2-phenoxyethylammonium bromide, hexadecylamine: chloride or bromide salt, dodecyl amine or chloride salt, and cetyldimethylethyl ammonium bromide or chloride), monoalkyldimethylbenzyl ammonium salts (examples include alkyldimethylbenzyl ammonium chlorides and benzethonium chloride as BTC), dialkyldimethyl ammonium salts (commercial products include domiphen bromide (DB), didecyldimethyl ammonium halides, and octyldodecyldimethyl ammonium chloride or bromide), heteroaromatic ammonium salts (commercial examples include cetylpyridium halides (CPC or bromide salt and hexadecylpyridinium bromide or chloride), cis-isomer 1-[3-chloroallyl]-3,5,7-triaza-1-azoniaadamantane, alkyl-isoquinolinium bromide, and alkyldimethylnaphthylmethyl ammonium chloride (BTC 1110). Polysubstituted quaternary ammonium salts, (commercially available products include, but are not limited to alkyldimethylbenzyl ammonium saccharinate and alkyldimethylethylbenzyl ammonium cyclohexylsulfamate), bis-quaternary ammonium salts (product examples include 1,10-bis(2-methyl-4-aminoquinolinium chloride)-decane, 1,6-bis{1-methyl-3-(2,2,6-trimethylcyclohexyl)-propyldimethyl ammonium chloride]hexane or triclobisonium chloride, and the bis-quat referred to as CDQ by Buckman Brochures), and polymeric quaternary ammonium salts (includes polyionenes such as poly[oxyethylene (dimethyliminio)ethylene(dimethyliminio)ethylene dichloride], poly[N-3-dimethylammonio)propyl]N-[3-ethyleneoxyethylenedimethylammonio) propyl]urea dichloride, and alpha-4||-tris(2-hydroxyethyle)ammonium chloride). As the skilled man will understand from U.S. Pat. No. 7,326,555, wherein several of these were shown to work and wherein it was shown that the skilled person can routinely find the appropriate concentrations for these compounds to selectively precipitate DNA, these are examples of SPAs, and based on the disclosure therein and the disclosure of the instant invention it is clear that these will also be suitable in the present invention.

In a preferred embodiment, cationic detergents are used in the present invention. In an even more preferred embodiment, dialkyldimethylammonium salts such as domiphen bromide (DB) are used in the present invention. Domiphen bromide is used as a selective precipitating agent for purification schemes which require the removal of any number of cellular components, especially nucleic acids, away from any number of different types of biological products, including but not limited to virus particles, virus-like particles or any other biological product which may be substantially separated from a contaminating culture-based component via a selective precipitation step. Though a large number of potential SPAs can be used to practice the present invention, domiphen bromide is of particular interest due primarily to its availability as a GMP grade raw material and current use in other products intended for human use. More specifically, since domiphen bromide is extensively used as an active ingredient in oral hygiene products as well as topical antibiotic cremes, this molecule is produced in large quantities and released under cGMP conditions.

The optimal SPA concentration that is used in high cell density suspensions for precipitating host cell DNA away from the cell suspension was determined herein. Although it was anticipated, based on the prior art, that adenovirus particles would immediately precipitate when being put in contact with high concentrations of SPA, unexpectedly, the adenovirus particles remained unprecipitated. Indeed, it was shown in the prior art, for instance in U.S. Pat. No. 7,326,555, that in low cell density suspensions (up to $1 \times 10^6$ cells/ml), adenovirus particles precipitate when the concentration of cationic detergent is increased. The suspension as produced by lysing high cell density cultures as disclosed herein will contain vastly increased amounts of host cell DNA and other impurities and will therefore need increased quantities of cationic detergent (e.g. increased by a factor 2.5). It is expected based on extrapolation of the results at low cell density, that this increase in cationic detergent concentration would lead to precipitation of the totality of the adenovirus particles present in the suspension.

Surprisingly, at high SPA concentrations, the selective removal of contaminating host cell DNA from a high cell density suspension containing adenovirus particles was still possible. In a preferred embodiment of the present invention, the SPA, preferably DB, is added to a concentration ranging from 1.2 to 5 mM. In an even more preferred embodiment the SPA, preferably DB, is added to a concentration ranging from 1.3 to 2.2 mM, e.g. 1.4 to 2 mM, e.g. 1.4 to 1.8 mM, e.g. 1.5 to 1.6 mM. Based on the present disclosure, it is clear that the skilled man in the art knows how to determine appropriate SPA concentration windows for a given cell density at harvest.

The appropriate concentration of DB for treating an adenovirus containing high cell density suspension comprising a cell density ranging between $10 \times 10^6$ and $150 \times 10^6$ cells/mL ranges between about 1.2 mM and 5 mM. The appropriate concentration of DB for treating an adenovirus containing high cell density suspension comprising a cell density ranging between $10 \times 10^6$ and $50 \times 10^6$ cells/mL ranges between about 1.3 mM and 2.2 mM. The appropriate concentration of DB for treating an adenovirus containing high cell density suspension harvest comprising a cell density ranging between $10 \times 10^6$ and $30 \times 10^6$ cells/mL ranges between about 1.3 and 2 mM, e.g. between about 1.4 and 1.9 mM, e.g. between about 1.4 and 1.8 mM, e.g. between about 1.4 and 1.7 mM, e.g. between about 1.45 and 1.65 mM, e.g. about 1.5-1.55 mM.

Nucleases (including but in no way limited to BENZONASE™, DNases, and RNases) are no longer required in this step but may still be beneficial for maximum DNA reduction. In view of the ability of this precipitation step to remove the vast majority of the contaminating nucleic acids, a later anion exchange chromatography (AEX) step may not be essential for product purity (depending on the final dosage). However, an AEX step may remain in the process for robustness.

It will be within the purview of the artisan to test potential substitutes for the SPAs disclosed herein to identify a compound which effectively precipitates nucleic acid molecules and other cellular debris away from adenovirus particles as exemplified herein for domiphen bromide (DB). Therefore, this present invention relates in part to methods of purifying adenovirus particles from a high cell density suspensions within which comprises selectively precipitating host cell nucleic acid molecules away from the adenovirus particles within the post-lysis high cell density suspension by adding a selective precipitation agent to the post-lysis host cell culture medium.

Clarification

The SPA-treated cell lysate obtained from the previous steps is subsequently clarified to remove precipitated impurities and cell debris. Said clarification can be performed by depth filtration. Centrifugation with or without polishing depth filtration also is feasible. Therefore, clarification of precipitated lysate may be accomplished using centrifugation alone, or centrifugation in tandem with a polishing clarification step such as depth filtration as described in U.S. Pat. No. 7,326,555.

In choosing a filter or filter scheme it was necessary to ensure a robust performance in the event upstream changes or variations occur. Maintaining the balance between good clarification performance and step yields can be investigated by testing a variety of filter types with varying internal media. Suitable filters may utilize cellulose filters, regenerated cellulose fibers, cellulose fibers combined with inorganic filter aids (e.g. diatomaceous earth, perlite, fumed silica), cellulose fibers combined with inorganic aids and organic resins, or any combination thereof, and polymeric filters (examples include but are not limited to nylon, polypropylene, polyethersulfone) to achieve effective removal and acceptable virus recoveries. In general a multiple stage process is preferable but not required. An exemplary two or three-stage process would consist of a coarse filter(s) to remove large precipitate and cell debris followed by polishing second stage filters(s) to with nominal pore sizes greater than 0.2 μm but less than 1 μm. The optimal combination will be a function of the precipitate size distribution as well as other variables. In addition, single stage operations employing a relatively tight filter or centrifugation may also produce a product of good quality. More generally, any clarification approach including dead-end filtration, microfiltration, centrifugation, or body feed of filter aids (e.g. diatomaceous earth) in combination with the dead-end or depth filtration, which provides a filtrate of suitable clarity to not foul the membrane and/or resin in the subsequent step, will be acceptable to practice within the present invention. Depth filtration shows a robust method of clarification for the present invention. Commercially available depth filter membranes are disclosed in U.S. Pat. No. 7,326,555 (column 14, line 65 through column 15, line 19), incorporated herein by reference.

The combination of the precipitation and clarification steps removes at least 70%, more likely at least 80%, or even preferably at least 90% of the host cell DNA away from the adenovirus particles after clarification (e.g. such as depth filtration alone or depth filtration combined with a polishing depth filtration step).

Methods of Further Purification

In certain embodiments, the harvested virus particles are further purified. Further purification of the virus can be performed in several steps comprising concentration, ultrafiltration, diafiltration or separation with chromatography as described in for instance WO 2005080556, incorporated herein by reference. Other steps, such as, anion exchange membrane chromatography, sterile filtration, reversed-phase adsorption, hydroxyapatite chromatography can also be used. These steps are for example disclosed in U.S. Pat. No. 7,326,555, incorporated in its entirety by reference herein. The person skilled in the art knows how to find the optimal conditions for each purification step. Also WO 98/22588, incorporated in its entirety by reference herein, describes methods for the production and purification of virus particles.

In certain embodiments according to the invention, the clarified adenovirus particle suspension can be treated by ultrafiltration. Ultrafiltration is used to concentrate the virus suspension. The suspension can be concentrated 5 to 20 times and possibly be treated with nuclease (as mentioned hereabove). Another aspect of the invention is the subsequent introduction of an exchange buffer via diafiltration. Diafiltration, or buffer exchange, using ultrafilters is a way for removal and exchange of salts, sugars and the like. The person skilled in the art knows under which conditions the buffer exchange shoud take place and which buffers are appropriate for this step.

The particular ultrafiltration membrane selected will be of a size sufficiently small to retain adenovirus particles but large enough to effectively clear impurities. Depending on the manufacturer and membrane type, nominal molecular weight cutoffs between 10 and 1000 kDa may be appropriate. Ultrafiltration using tangential flow mode is preferred. In said mode, the step may be controlled by setting a fixed cross-flow with or without backpressure on the retentate return, setting a fixed transmembrane pressure, or fixing both the cross-flow and the permeate flux.

Nuclease treatment can also be considered for inclusion in the process at this point, but is by no means required. Nuclease treatment can include the use of a broad spectrum nuclease (e.g. BENZONASE™), a DNase, a RNase, or any combination thereof. A nuclease or cocktail with both RNase and DNase activity is preferred. A nuclease treatment step can be contemplated at any point in the process, as long as residual nuclease content in the final product is acceptable to the application. It is preferred that the nuclease treatment occur after clarification and especially preferred that nuclease treatment occur after clarification and a concentration step, but before an anion exchange chromatography step.

According to the invention, a following step can be an anion exchange chromatography step. During said step adenovirus particles are bound to a positively charged material, e.g. a membrane, cartridge or column. Subsequent elution allows for separating the virus particles from impurities and remaining host cell DNA.

For adenovirus purification with a Mustang Q membrane absorber, the NaCl concentration for loading and washing could presumably be anywhere from 0.3 to 0.4 M at pH 7.5 and would shift at alternating pH's. More preferably the NaCl concentration is 0.35 M. The pH of the buffers needs to be high enough for adenovirus to bind (greater than approximately 6.5). In addition, the pH of the buffer system should also be low enough to avoid viral instability. The precise maximum pH which is usable will depend on the specific stability profile of the adenovirus and the buffer components, and can easily be determined by the skilled man in the art for that particular application. As a guide and certainly not a limitation, the pH could potentially range from about 5-10.

The presence of 0.1% PS-80 in the buffers is highly preferred to achieving low residual DNA levels in the product because it attenuates adenovirus/DNA association and adenovirus aggregation. It will be within the realm of routine experimentation for the person skilled in the art to establish higher or lower detergent concentrations or alternative detergents which would be useful to promote dissociation of adenovirus particles away from other adenovirus as well as various cell contaminants. It is also within this same realm of experimentation that the person skilled in the art may choose an alternative detergent to the process buffer. Examples for such alternative detergents can be found in U.S. Pat. No. 7,326,555. Anion exchange membrane chromatography products such as those produced by Pall (e.g. Mustang™ series) and Sartorius (e.g. Sartobind series) are suitable for virus purification according to the present invention. U.S. Pat. No. 6,485,958 or WO 05/080556 describe the use of anion exchange chromatography for purification of recombinant adenovirus.

The binding capacity for virus on a membrane absorber such as Mustang Q (Pall Corporation) is extremely high, and in the order of $7 \times 10^{13}$ VP/ml. Other membrane absorbers and resins that are suitable for virus purification in this process include but are in no way limited to Source 15Q and Source 30Q (GE life sciences), Q-Sepharose XL (GE life sciences), Fractogel TMAE (EM industries), Sartobind Q (Sartorius), Adsept Q (Natrix separations), CIM QA (BIA separations). Adenovirus elution would preferably be performed using a buffer containing NaCl. The skilled person knows how to optimize the NaCl concentration.

In certain embodiments, it is preferred to use at least one anion exchange chromatography step. After the anion exchange chromatography step, the adenovirus may be sufficiently pure. In certain embodiments however a size exclusion chromatography step is further performed to increase the robustness of the process. This step may be prior to or after the anion exchange chromatography step. Obviously, other purification steps may also be suitably combined with an anion exchange chromatography step. The use of anion exchange chromatography for adenovirus purification has been extensively described, and this aspect is therefore well within the reach of the person skilled in the art. Many different chromatography matrices have been employed for purification of adenovirus and are suitable. The person skilled in the art can easily find the optimal anion exchange material for purifying said adenovirus.

In any particular embodiment of the present invention, the anion exchange product can be diafiltered into formulation buffer and sterile filtered. Alternatively, an additional chromatography step (e.g. cation exchange) may be added either before or after the diafiltration with the potential to improve the robustness of impurity and/or virus/prion clearance.

An additional ultrafiltration step could also be possible at this stage. Tangential flow ultrafiltration is useful in removing residual protein and nucleic acid and to exchange the adenovirus into a formulation buffer. The choice between 300 kDa and 500 kDa membranes is dictated by the tradeoffs between yield and improved impurity clearance. Other membrane configurations (such as a hollow fiber) are acceptable substitutes. The selected ultrafiltration membrane will be of a size sufficiently small to retain adenovirus particles but large enough to effectively clear impurities. Depending on the manufacturer and membrane type, nominal molecular weight cutoffs between 100 and 1000 kDa may be appropriate.

A sterile filtration step may be included in the process, which is helpful in eliminating bioburden. The product can be filtered through a 0.22 micron modified polyvinylidene fluoride (PVDF) membrane (e.g. Millipore Millipak).

Optional downstream processing steps could be added in the process. These could e.g. include a size exclusion chromatography step, a reversed-phase adsorption step and/or a hydroxyapathite chromatography step. More details on each of these steps can be found in e.g. U.S. Pat. No. 7,326,555, WO 03/097797, WO 02/44348.

International application WO 97/08298 describes the purification of adenoviruses using certain chromatographic matrices to prevent damage to the viruses, including anion exchange and size exclusion steps.

Certain ultrafiltration methods are also very suitable for purification of adenovirus, as disclosed in WO 2006/108707. Such steps may be performed in addition to or instead of certain chromatographic purification steps.

Scale of Cell Culture Systems and Down Stream Processing Systems

The processes of the present invention are scalable. The cell cultures used in the present invention range from small scale cultures (e.g. 1-10 liter runs) to medium scale cutures (e.g. 20-1000 L runs) up to large commercial scale preparations, such as 1000 to 50 000 L production runs. The initial process steps (lysis, depth filtration and ultrafiltration) scale with culture volume while the anion exchange chromatography and subsequent steps scale with adenoviral particle input. Therefore, the size of the latter steps will be based on a bioreactor productivity estimate of at least $1 \times 10^{12}$ adenovirus particles per mL (vp/mL). These high adenovirus yields can for instance be obtained by infecting high cell density cultures (as described e.g. in EP08168181.9). The further purification of these high density cell suspensions containing high concentrations of adenovirus particles is made possible with the present invention. The possibility to process these suspensions, which contain high amounts of cell debris and host cell DNA allow for the purification of high quantities of adenovirus particles per volume of suspension. It is the merit of this invention to provide for a method for processing cell culture batches with high cell densities, containing high concentrations of adenovirus particles and therewith allowing for very high adenovirus yields per processed volume. The present method, although it is applicable to large scale cell cultures will allow for cells to be cultured at smaller scale, yet to higher cell densities and still reach high adenovirus yields which can efficiently be further processed. This method offers the possibility to process highly concentrated adenovirus batches which will have a great impact on the entire adenovirus purification industry.

Adenovirus and Producer Cells

The invention relates to purification of adenovirus. An adenovirus according to this invention can be any wild type, modified, mutated adenovirus and/or recombinant adenoviral vector. Of specific interest in gene vaccination and/or gene therapy applications is the use of a $1^{st}$ or $2^{nd}$ generation replication incompetent adenovirus, crippled by E1 or further deletions, including "gutless" adenovirus vectors. The adenovirus genome is generally associated with benign pathologies in humans. The genome is amenable to manipulation, depending on the strategy utilized to construct the respective vector. A replication-incompetent virus such as an recombinant adenovirus 35 (rAd35) or 26 (rAd26) vector (as exemplified herein) requires a producer cell line which complements the deletions.

A producer cell (sometimes also referred to in the art and herein as 'packaging cell' or 'complementing cell' or 'host cell') can be any producer cell wherein a desired adenovirus can be propagated. For example, the propagation of recombinant adenovirus vectors is done in producer cells that complement deficiencies in the adenovirus. Such producer cells preferably have in their genome at least an adenovirus E1 sequence, and thereby are capable of complementing recombinant adenoviruses with a deletion in the E1 region. Further the adenovirus may have a deletion in the E3 region, which is dispensable from the Ad genome, and hence such a deletion does not have to be complemented. Any E1-complementing producer cell can be used, such as human retina cells immortalized by E1, e.g. 911 or PER.C6 cells (see U.S. Pat. No. 5,994,128), E1-transformed amniocytes (See EP patent 1230354), E1-transformed A549 cells (see e.g. WO 98/39411, U.S. Pat. No. 5,891,690), GH329:HeLa (Gao et al, 2000, Human Gene Therapy 11: 213-219), 293, and the like. In certain embodiments, the producer cells are for instance HEK293 cells, or PER.C6 cells, or 911 cells, or IT293SF cells, and the like. Preferably PER.C6 cells (ECACC deposit no. 96022940, deposited on 29 Feb. 1996 at the ECACC, CAMR, Porton Down, Salisbury SP4 OJG, United Kingdom; see U.S. Pat. No. 5,994,128), or cells derived therefrom are used as producer cells.

The replication-deficient adenoviral vector can be generated by using any species, strain, subtype, or mixture of species, strains, or subtypes, of an adenovirus or a chimeric adenovirus as the source of vector DNA (see for instance WO 96/26281, WO 00/03029), which for instance may provide the adenoviral vector with the capability of infecting certain desired cell types. In a preferred embodiment of the present invention, rAd35 or rAd26 is used as an adenovirus.

The person skilled in the art will be aware of the possibilities to propagate adenoviral vectors of different serotypes on specific host cells, using methods such as for instance disclosed in U.S. Pat. No. 6,492,169 or in WO 03/104467, and references therein. For instance, for propagation of E1-deficient rAd35, specific producer cells that express E1B-55K of Ad35 can be constructed, for instance based on existing producer cells that express E1A and E1B of Ad5 such as PER.C6 or HEK293 cells (see, e.g. U.S. Pat. No. 6,492,169), as is known to the skilled person. Alternatively and preferably, existing (Ad5-) complementing cell lines such as for instance PER.C6 or HEK293 can be used without modification of the cells for propagation of E1-deficient rAd35 or rAd26, by inclusion of the E4-orf6 coding sequence of Ad5 into the rAd35 or rAd26 vector, as extensively disclosed in for instance WO 03/104467, incorporated in its entirety by reference herein. Thus, propagation of adenoviral vectors of any serotype can be done on producer cells using means and methods well known to the person skilled in the art. Adenoviral vectors, methods for construction thereof and methods for propagating thereof, are well known in the art and are described in, for example, U.S. Pat. Nos. 5,559,099, 5,837, 511, 5,846,782, 5,851,806, 5,994,106, 5,994,128, 5,965,541, 5,981,225, 6,040,174, 6,020,191, and 6,113,913, and Thomas Shenk, "Adenoviridae and their Replication", M. S. Horwitz, "Adenoviruses", Chapters 67 and 68, respectively, in Virology, B. N. Fields et al., eds., 3d ed., Raven Press, Ltd., New York (1996), and other references mentioned herein.

The invention is further explained in the following examples. The examples do not limit the invention in any way. They merely serve to clarify the invention.

EXAMPLES

Example 1

Selective Host Cell DNA Precipitation in High Cell Density Suspensions

Selective host cell DNA precipitation was demonstrated in the prior art (Goerke et al, U.S. Pat. No. 7,326,555) for cell densities up to $1 \times 10^6$ cells/ml. It was shown therein that (at low cell densities) at least 80% of the host cell DNA was precipitated away from the cell suspension with a 90% recovery of virus particles. However, it was hitherto completely unknown if such selective precipitation would be feasible at high cell density, since such cell suspensions would contain much higher amounts of host cell DNA and cell debris, and therefore it would be expected that much higher amounts of DNA precipitating agent would be required, whereas extrapolation of the data from the prior art would suggest that such higher concentrations of DNA precipitating agent would also precipitate the adenovirus.

In order to explore the possibility of DNA precipitation at high cell densities, host cell DNA precipitation was tested in small scale test tubes containing cell densities up to $30 \times 10^6$ cells/ml. The small scale test tube model was used as a quick screening tool to test whether selective DNA precipitation still occurs at high cell densities.

PER.C6 cells were grown in a bioreactor and infected with Adenovirus 35 (Ad35) and grown at 37° C. in serum-free culture medium for 3 days. Cells were harvested at a cell density between 2 and $30 \times 10^6$ cells/ml. and virus titers ranging from $8 \times 10^{10}$ to $1.5 \times 10^{12}$ VP/ml. Cell lysis was performed over a period of 2 to 24 hours (hrs), by adding the nonionic detergents Triton X-100 and Tween-80 to final concentrations of 0.1% and 0.05% respectively. Incrementing concentrations of Domiphen Bromide (DB) in 40 mM NaCl were added to 3.5 ml of lysed harvest, followed by immediate vortexing for 1 minute. The precipitated material was removed with 0.45 μm polyvinylidene fluoride (PVDF) syringe filters. The filtrates were analyzed for Ad35 and host cell DNA concentrations using a HPLC-AEX and Q-PCR assay respectively.

FIG. 1 shows the virus recovery and precipitated host cell DNA, plotted against the Domiphen Bromide concentration. The curves depicted in triangles are obtained from cell culture harvests having cell densities ranging between $2.5 \times 10^6$ and $3.5 \times 10^6$ cells/ml. The curves depicted in circles are obtained from cell culture harvests having cell densities ranging between $20 \times 10^6$ and $30 \times 10^6$ cells/ml. The C* (Domiphen Bromide concentration which shows 90% virus recovery) at low and high cell densities and the related percentage of precipitated host cell DNA are highlighted on the graphs.

The DB concentration that is required to precipitate more then 90% of the host cell DNA at cell densities ranging between $20 \times 10^6$ and $30 \times 10^6$ cells/ml is increased by a factor of at least 2.5 times compared to the DB concentration required at cell densities that are 10 times lower. Surprisingly, the increased DB concentration did not precipitate the virus particles, as would be expected from extrapolation of the curves obtained at lower cell density.

Figure 2:
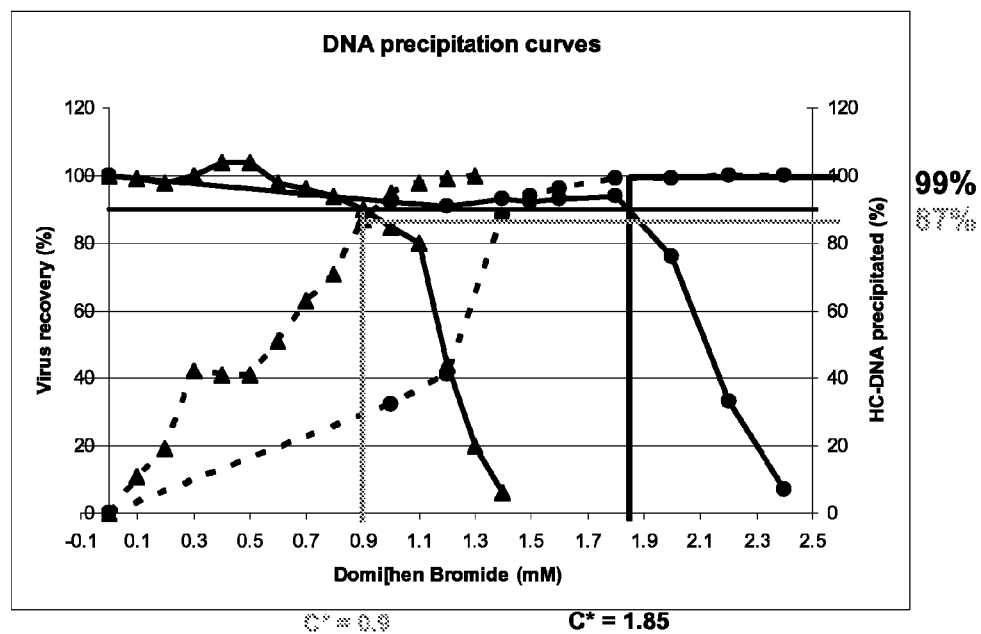
FIG. 2. Adenovirus recovery and precipitated host cell DNA, plotted against the domiphen bromide concentration in low ($2.5\times10^6$-$3.5\times10^6$ vc/ml) and high ($18\times10^6$-$25\times10^6$ vc/ml) density cell suspensions.

The experiment was repeated with cell culture harvests having cell densities ranging between $18 \times 10^6$ and $25 \times 10^6$ cells/ml. FIG. 2 shows the virus recovery and precipitated host cell DNA, plotted against the Domiphen Bromide concentration. The curves depicted in triangles are obtained from cell culture harvests having cell densities ranging between $2.5 \times 10^6$ and $3.5 \times 10^6$ cells/ml. The curves depicted in circles are obtained from cell culture harvests having cell densities ranging between $18 \times 10^6$ and $25 \times 10^6$ cells/ml. The C* (Domiphen Bromide concentration which gives 90% virus recovery) at low and high cell densities and the related percentage of precipitated host cell DNA are highlighted on the graphs.

As can be noted from the graphs in FIGS. 1 and 2, the DB concentration which gives 90% virus recovery (C*) for high cell density suspensions may slightly differ between individual experiments, and this is part of the normal variation. However, the graphs consistently demonstrate that a selective prepipitation of DNA is possible also at high cell densities, and that the suitable concentration of SPA (here DB) is significantly higher than for the low cell density cultures, but much lower than would be expected based on extrapolation. Thus, the skilled person will recognize that there is a range rather than a fixed point of suitable concentrations for the selective precipitating agent, and based upon the disclosure herein can find the suitable range. For instance, appropriate concentrations of DB for treating an adenovirus containing high cell density suspension harvest comprising a cell density ranging between about $10 \times 10^6$ and $30 \times 10^6$ cells/mL range between about 1.3 and 2 mM.

Based on these results, the person skilled in the art will now be aware that DNA precipitation can be extrapolated to adenovirus containing suspensions containing even higher cell densities, e.g. of about $40 \times 10^6$ cells/mL, e.g. of about $50 \times 10^6$ cells/mL, e.g. up to about $100 \times 10^6$ cells/mL, e.g. up to about $150 \times 10^6$ cells/mL, and that adenovirus from such high cell density suspensions can be purified with the process from the present invention.

Example 2

Selective Host Cell DNA Precipitation in High Cell Density Suspensions at Larger Scale DNA precipitation was tested at scales ranging between 0.5 L and 20 L. The DB concentrations used for DNA precipitation were based on the previous experimental results (FIG. 2). About 80% of the C* concentration as determined in the small scale test tube model was used.

PER.C6 cells were cultured either in batch or in perfusion mode in 2 L or 10 L bioreactors. In batch mode, cells were cultured during 4 days and infected after they reached a density ranging between $1 \times 10^6$ to $1.6 \times 10^6$ cells/ml. After infection, the cells were cultured further during 3 days and were harvested.

In perfusion mode, the perfusion which was performed with an ATF system, was started 4 days post inoculation at a cell density of approximately $2.5 \times 10^6$ total cells/mL. After 14 days of perfusion the cell suspension was diluted with fresh serum free medium in the bioreactor to a cell density of about $13 \times 10^6$ cells/mL. Subsequently the bioreactor was infected with Ad35 virus. The ATF system was started 5 hours post infection at a medium refreshment rate of 2 vessel volumes per day. After 3 days (post infection) the cells were harvested. The cell density at harvest (CDAH) is given in Table 1.

Subsequent to harvest, cells were lysed over a period of 2 to 24 hours by adding the nonionic detergents Triton X-100 and Tween-80 to final concentrations of respectively 0.1 and 0.05%. Thereafter, Domiphen Bromide was added to the lysed harvest to final concentrations of 0.72 and 1.52 mM in 40 mM NaCl. The precipitated lysate was clarified using two charged depth filters with estimated pore sizes between ~10-~5 µm (Millistak+CE20) and ~1-~0.2 µm (Cuno Zeta plus 50CP) respectively. The clarification was performed at a constant flux of 100 LMH (liter per square meter per hour) until the pressure reached 5 psi.

Table 1 shows the process parameters and results of the purification process. Lysis, DNA precipitation (DNA ptt) and clarification were performed using 8 different harvests, which differed in volume, cell density at harvest (CDAH) and virus titer. The harvests were taken from 2 L or 10 L bioreactors. The percentage of precipitated host cell DNA (HC-DNA) and the virus recovery over the precipitation step were determined.

TABLE 1

| | Process parameters | | | Results | | |
|---|---|---|---|---|---|---|
| | | | | DNA ppt | Clarification | |
| Exp. # | CDAH ($\times 10^6$ cells/ml) | Virus titer ($\times 10^{11}$ VP/ml) | DB (mM) | Step recovery (%) | Step recovery (%) | HC-DNA reduction (%) |
| 1 | 1.36 | 2.13 | 0.72 | 92 | 86 | 99.6 |
| 2 | 2.47 | 2.24 | | 91 | 86 | 99.9 |
| 3 | 2.37 | 1.85 | | 90 | 90 | 99.2 |
| 4 | 9.1 | 6.7 | 1.52 | 69 | 97 | 99.9 |
| 5 | 18.6 | 8.9 | | 88 | 98 | 99.8 |
| 6 | 20.1 | 15 | | 90 | 82 | 98.3 |
| 7 | 16.7 | 11 | | 99 | 71 | 99.9 |
| 8 | 25.8 | 15.9 | | 104 | 92 | 99.8 |

It is concluded that selective DNA precipitation is possible at high cell density. Indeed, although the DB concentration was increased (with a factor 2), the virus particles remained unprecipitated (see recovery higher than 69%) and the HC-DNA reduction was higher than 98%.

Herewith it allows for the processing of large volumes of high cell density suspensions, which is needed in industrial processes.

It must be noted that for practical reasons, a single DB concentration (1.52 mM) has been used for selective DNA precipitation in experiments 4-8. Said experiments show that adenovirus containing suspensions having a broad range ($9.1 \times 10^6$-$25.8 \times 10^6$ vc/ml) of cell densities can be treated with 1.52 mM of DB. This is consistent with the notion above that the relationship between suitable concentrations of selective precipitating agent and cell density is not a very fixed one, but rather provides for variation so that a range of concentrations of precipitating agent is suitable for a given cell density.

The appropriate concentration of DB for treating an adenovirus containing high cell density suspension comprising a cell density ranging between $10 \times 10^6$ and $50 \times 10^6$ cells/mL ranges between about 1.3 mM and 2.2 mM. The appropriate concentration of DB for treating an adenovirus containing high cell density suspension harvest comprising a cell density ranging between $10 \times 10^6$ and $30 \times 10^6$ cells/mL ranges between about 1.3 and 2 mM.

REFERENCES

Cortin V, Thibault J, Jacob D, Garnier A. High-Titer Adenovirus Vector Productioni in 293S Cell Perfusion Culture. Biotechnol. Prog. 2004.

Goerke A, To B, Lee A, Sagar S, Konz K. Development of a Novel Adenovirus Purification Process Utilizing Selective Precipitation of Cellular DNA. Biotechnology and bioengineering, Vol. 91, No. 1, Jul. 5, 2005.

Yuk I H Y, Olsen M M, Geyer S, Forestell S P. Perfusion Cultures of Human Tumor Cells: A Scalable Production Platform for Oncolytic Adenoviral Vectors. Biotechnol. Bioengin. 86: 637-641 (2004).

The invention claimed is:

1. A method for purifying adenovirus particles from a suspension of producer cells having a cell density between about $10 \times 10^6$ and $50 \times 10^6$ cells/mL, the method comprising the steps of:
   (a) infecting a producer cell suspension having a cell density between about $10 \times 10^6$ and $50 \times 10^6$ cells/mL with adenovirus, and culturing the producer cells;
   (b) lysing with detergent the producer cells within the cell suspension having a cell density between about $10 \times 10^6$ and $50\times10^6$ cells/mL, to produce a suspension comprising adenovirus particles; then
(c) selectively precipitating producer cell DNA away from the adenovirus particles by adding domiphen bromide (DB) to the suspension to a final concentration within the range of 1.3 to 2.2 mM; and then
(d) clarifying the suspension comprising adenovirus particles to obtain a purified adenovirus-containing suspension,
wherein at least 80% of producer cell DNA is precipitated away from the suspension comprising adenovirus particles, wherein steps (b), (c) and (d) are performed consecutively.

2. The method according to claim 1, wherein the cell suspension has a cell density between about $10\times10^6$ and $30\times10^6$ cells/mL, and wherein the final concentration of domiphen bromide is within the range of 1.3 to 2 mM.

3. The method according to claim 1, wherein the method further comprises an anion-exchange step and an ultrafiltration step.

4. The method according to claim 2, wherein the method further comprises an anion-exchange step and an ultrafiltration step.

5. A method for purifying adenovirus particles from a suspension of producer cells having a cell density between about $10\times10^6$ and $50\times10^6$ cells/mL, the method comprising the steps of:
(a) infecting a producer cell suspension having a cell density between about $10\times10^6$ and $50\times10^6$ cells/mL with adenovirus, and culturing the producer cells;
(b) lysing with detergent the producer cells within the cell suspension having a cell density between about $10\times10^6$ and $50\times10^6$ cells/mL, to produce a suspension comprising adenovirus particles;
(c) selectively precipitating producer cell DNA away from the adenovirus particles by adding domiphen bromide (DB) to the suspension of step (b) to a final concentration within the range of 1.3 to 2.2 mM; and
(d) clarifying the suspension of step (c) to obtain a purified adenovirus-containing suspension,
wherein at least 80% of the producer cell DNA is precipitated away from the suspension.

6. The method according to claim 5, wherein the producer cell suspension has a cell density of from about $10\times10^6$ to $30\times10^6$ cells/mL, and the final DB concentration is from 1.3 to 2 mM.

7. The method according to claim 5, wherein the method further comprises:
an anion-exchange step; and
an ultrafiltration step.

8. The method according to claim 6, wherein the method further comprises:
an anion-exchange step; and
an ultrafiltration step.

9. A method for purifying adenovirus particles from a suspension of producer cells having a cell density between about $10\times10^6$ and $50\times10^6$ cells/mL, wherein the method comprises:
(a) infecting a producer cell suspension having a cell density between about $10\times10^6$ and $50\times10^6$ cells/mL, and culturing the producer cells;
(b) removing at least 80% of producer cell DNA from the suspension of producer cells having a cell density between about $10\times10^6$ and $50\times10^6$ cells/mL, by a DNA precipitation step consisting essentially of lysing with detergent the producer cells within the cell suspension, selectively precipitating producer cell DNA away from the adenovirus particles by adding domiphen bromide (DB) to the suspension to a final concentration within the range of 1.3 to 2.2 mM, and clarifying the suspension, to obtain a suspension comprising adenovirus particles.

10. The method according to claim 9, wherein the method further comprises at least one step after the DNA precipitation step selected from the group consisting of concentration of the adenovirus particles; sterile filtration; ultrafiltration; diafiltration; chromatography; anion exchange chromatography; hydroxyapatite chromatography; reversed-phase adsorption; and nuclease treatment.

11. The method according to claim 9, wherein the method comprises in the following order:
removing by DNA precipitation at least 80% of producer cell DNA from the suspension of producer cells having a cell density between about $10\times10^6$ and $50\times10^6$ cells/mL;
concentrating the adenovirus particles;
nuclease treatment; and
anion exchange chromatography.

* * * * *